United States Patent [19]

Vinegar et al.

[11] 4,322,411

[45] Mar. 30, 1982

[54] ANTI-INFLAMMATORY NUCLEOSIDES

[75] Inventors: Ralph Vinegar, Chapel Hill; Gerald Wolberg, Cary, both of N.C.

[73] Assignee: Burroughs Wellcome Co., Research Triangle Park, N.C.

[21] Appl. No.: 143,833

[22] Filed: Apr. 25, 1980

[51] Int. Cl.³ ............................................. A61K 31/70
[52] U.S. Cl. ..................................... 424/180; 536/24; 536/26
[58] Field of Search ..................... 424/180; 536/26, 24

[56] References Cited

U.S. PATENT DOCUMENTS

| 4,148,888 | 4/1979 | Cantoni et al. | 424/180 |
| 4,210,639 | 7/1980 | Chiang et al. | 536/24 |

FOREIGN PATENT DOCUMENTS

| 10668 | 12/1979 | European Pat. Off. | 424/180 |

OTHER PUBLICATIONS

Mizuno, et al. "Chem. Abst.", vol. 70, p. 47771(n), 1969.

*Primary Examiner*—Johnnie R. Brown
*Attorney, Agent, or Firm*—Donald Brown

[57] ABSTRACT

3-Deazaadenosine and its pharmaceutically acceptable salts are potent anti-inflammatory agents.

10 Claims, No Drawings

ANTI-INFLAMMATORY NUCLEOSIDES

The present invention is concerned with compounds useful in medicine. More specifically it is concerned with the treatment of inflammation by the administration of an adenosine analogue.

United States Pat. No. 4,148,888 discloses 3-deazaadenosine, 4-amino-1-β-D-ribofuranosyl-1H-imidazo[4,5-c]-pyridine, as an antiviral and antifocal agent.

United Kingdom patent application No. 40447/78 discloses 3-deazaadenosine as an immunosuppresant.

3-Deazaadenosine has now been surprisingly found to possess anti-inflammatory activity and is thus useful in the treatment of inflammation and thus disease conditions associated with inflammation.

The invention accordingly provides a method for the treatment of inflammation in mammals including humans suffering from an inflammatory condition, which comprises the administration of an anti-inflammatory, non-toxic amount of 3-deazaadenosine or a pharmaceutically acceptable salt thereof.

By the term 'inflammation' is meant the reactive state of hyperaemia and exudation from its blood vessels, with consequent redness, heat, swelling and pain, which a tissue enters in response to physical or chemical injury or bacterial invasions.

Clinical conditions with which inflammation is associated, and hence for which an anti-inflammatory agent is indicated, include for example arthritis, including rheumatoid arthritis and osteoarthritis, post operative inflammation, dental inflammation, acute and chronic ocular inflammatory diseases, conjunctivitis.

3-Deazaadenosine has been found to be a potent, long-acting anti-inflammatory agent and is effective orally, systemically and locally. 3-Deazaadenosine is useful in the treatment of both acute and chronic inflammation. 3-Deazaadenosine has been found to inhibit both developing and established adjuvant arthritis, an animal model in the rat of human rheumatoid arthritis, and is thus particularly useful in the treatment of acute and chronic rheumatoid arthritis.

The mechanism of the anti-inflammatory action of 3-deazaadenosine is at present unknown. It is not antipyretic and has not analgesic activity per se, and in this respect is like steroidal anti-inflammatory drugs such as prednisolone and hydrocortisone and like these known drugs will give relief from pain in many clinical syndromes by reducing inflammation. 3-Deazaadenosine does not inhibit prostaglandin metabolism in vitro through either the lipoxygenase or cyclooxygenase pathway and is thus free of the side effects, particularly gastric damage and inhibition of platelet aggregation, associated with prostaglandin inhibitors such as aspirin. 3-Deazaadenosine is also free of the side effects of the anti-inflammatory steroids and unlike compounds such as acetaminophen (paracetamol) does not cause liver damage in the animal models used.

Although its mechanism of action is different to that of aspirin, 3-deazaadenosine is similar to aspirin in that it has a long duration of action (about 15 hours) associated with a short half life. Thus 3-deazaadenosine will require relatively infrequent administration for example twice daily and the problem of morning stiffness and associated pain and crippling effects in patients with arthritic conditions may be alleviated, in contrast to the shorter acting non-steroidal and steroidal anti-inflammatory agents which do not possess this property. In addition 3-deazaadenosine, by virtue of its different mode of action to aspirin, salicylates and steroids, may be combined with such drugs to provide a 'sparing effect' reducing the required dose of these drugs and hence the side effects associated therewith. 3-Deazaadenosine is also advantageous in possessing a high therapeutic index and thus is unlikely to present problems associated with accidental overdose. Its high water solubility is a yet further advantage.

The amount of 3-deazaadenosine required to reduce inflammation is relatively low and lies in the range of about 0.1 to about 30 mg/kg per day, particularly about 0.2 to about 5 mg/kg per day, preferably about 0.3 to about 1 mg/kg per day.

In contrast immunesuppression requires more than 30 mg/kg and antiviral activity requires 100–200 mg/kg per day. Thus effects associated with other activities of 3-deazaadenosine, in particular suppression of the immune response, are expected to be absent or minimal at the dose range required for anti-inflammatory activity.

As 3-deazaadenosine is effective for both chronic and acute, i.e. both long and short term, inflammation, the compound may be administered for as long as the inflammation remains, which may be for several hours to a number of years.

When 3-deazaadenosine is administered in the form of a pharmaceutically acceptable salt then the salt will be a non-toxic salt, suitably an acid addition salt. Suitable salts include those derived from hydrochloric acid, hydroiodic acid, sulphuric acid, phosphoric acid, acetic acid, p-toluene sulphonic acid, methane sulphonic acid, maleic acid, lactic acid, citric acid, tartaric acid, succinic acid, oxalic acid, p-chlorobenzenesulphonic acid, isethionic acid, glucuronic acid, pantothenic acid, and lactobionic acid.

While it is possible for 3-deazaadenosine or a pharmaceutically acceptable salt thereof (hereinafter referred to as "the active compounds") to be administered as the raw chemical it is preferably presented in the form of a pharmaceutical formulation.

A pharmaceutical formulation will comprise an active compound together with a pharmaceutically acceptable carrier therefor. The carrier must be "acceptable" in the sense of being compatible with the other ingredients of the formulation and not deleterious to the recipient thereof. The pharmaceutical formulations may be prepared by any of the methods well known in the art of pharmacy all of which involve bringing the active compound into association with the carrier therefor.

3-Deazaadenosine is effective as an anti-inflammatory agent not only orally and systemically but also locally and is thus particularly suitable for topical administration. The term "topical" as applied herein relates to the use of the active ingredient incorporated in a suitable pharmaceutical carrier, and applied at the site of the disease for the exertion of local action. Included within the scope of topical formulations are ophthalmic formulations.

Pharmaceutical formulations suitable for topical administration may be presented in anhydrous forms such as lotions, jellies, sprays, aerosols, bath oils or preferably ointments. The term ointment includes formulations (including creams) having oleaginous, absorption, water-soluble and emulsion type bases, for example petrolatum, lanolin, polyethylene glycols and mixtures thereof. Ointments are semi-solid materials with the active compound dispersed therein. These and other topical formulations enable the active ingredient to be applied and retained locally at the site of the disease.

Topical formulations may contain a concentration of the active compound of from about 0.01 to about 10% w/w preferably about 0.1 to about 1% w/w most preferably about 0.2 to about 0.5% w/w. Topical formulations may be applied locally one or more times daily, as required.

Other pharmaceutical formulations include those suitable for oral, rectal, and parenteral administration although of these oral is preferred. The formulations may, where appropriate, be conveniently presented in discrete dosage units and may be prepared in any of the methods well known in the art of pharmacy. A convenient unit dose formulation contains the active compound in an amount of from 5 mg to 250 mg, preferably 10 to 100 mg, most preferably about 50 mg to be taken once or several times daily.

All methods for the preparation of such formulations include the step of bringing into association the active compound with liquid carriers or finely divided solid carriers or both and then, if necessary, shaping the products into the desired formulation.

Pharmaceutical formulations suitable for oral administration wherein the carrier is a solid are mostly preferably presented as unit dose formulations such as boluses, capsules, cachets or tablets each containing a predetermined amount of the active compound. A tablet may be made by compression or moulding, optionally with one or more accessory ingredients. Compressed tablets may be prepared by compressing in a suitable machine the active compound in a free-flowing form such as a powder or granules optionally mixed with a binder, lubricant, inert diluent, lubricating; surface active or dispersing agent. Tablets may be optionally coated and, if uncoated, may be optionally scored. Capsules may be prepared by filling the active compound either alone or in admixture with one or more accessory ingredients, into the capsule cases and then sealing them in the usual manner. Cachets are analogous to capsules wherein the active ingredients together with any accessory ingredient(s) are sealed in a rice paper envelope.

Pharmaceutical formulations suitable for oral administration wherein the carrier is a liquid may be presented as a solution or a suspension in an aqueous liquid, or as an oil-in-water or water-in-oil liquid emulsion.

Pharmaceutical formulations suitable for rectal administration wherein the carrier is a solid are most preferably presented as unit dose suppositories.

Suitable carriers include coca butter and other material commonly used in the art, and the suppositories may be conveniently formed by admixture of the active compound with the softened or melted carrier(s) followed by chilling and shaping in moulds.

Pharmaceutical formulations suitable for parenteral administration include sterile solutions or suspensions of the active compound in aqueous or oleaginous vehicles. Such preparations are conveniently presented in unit dose or multidose containers which are sealed after introduction of the formulation until required for use.

It should be understood that in addition to the aforementioned carrier ingredients the pharmaceutical formulations described above may include, as appropriate, one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

The invention will now be illustrated by the following Examples which should in no way be considered as a limitation thereof.

EXAMPLE 1

Acute Anti-inflammatory Activity of 3-Deazaadenosine: Carrageenan Pleurisy Assay (CPA)

Following the procedure previously described by Vinegar et al. in Proc. Soc. Exp. Biol. Med., 143, 711 (1973) and recently modified (Vinegar et al., Eur. J. Rheum. Inflam. 1, 204 (1978)) the acute anti-inflammatory activity of 3-deazaadenosine was compared with that of known anti-inflammatory drugs. The average 3 hr exudate volume for each drug-treated group was determined and the % inhibition relative to solvent-fed control animals calculated, the $ED_{50}$ (mg/kg of body wt) being the dose required to reduce the 3 hr exudate volume by 50%. There were 5 animals in each drug-treated group and the control group. The results are shown in Table I:

TABLE I

| | $ED_{50}$ (mg/kg) | | | |
|---|---|---|---|---|
| | 3-Deaza-adenosine | Aspirin | Hydro-cortisone | Prednisolone |
| 3 hr. Vol. p.o. | 2.8 + 0.65 | 28 + 3.2 | 14 + 10.2 | 3.0 + 0.50 |

EXAMPLE 2

Duration of action of anti-inflammatory activity of 3-deazaadenosine

By means of the Carrageenan Pleurisy Assay of Example 1 the duration of action of the test compounds after a single oral pretreating dose was determined. For 3-deazaadenosine the effect lasted for 14.9 hours at 6 mg/kg (p.o.) whilst for aspirin (150 mg/kg p.o.) and acetaminophen (220 mg/kg p.o.) the effect lasted 35 hours and 2 hours, respectively. This value represents the time (hours) of drug administration prior to the injection of carrageenan in which the inhibition of the 3 hour pleural exudate volume declined to 40%.

EXAMPLE 3

Local Anti-Inflammatory Activity of 3-Deazaadenosine: Carrageenan Pleurisy Assay (CPA)

Following the procedure described by Vinegar et al., Eur. J. Rheum. Inflam. 1, 204 (1978) the local anti-inflammatory activity of 3-Deazaadenosine was determined and compared to that of standard anti-inflammatory drugs. There were 5 animals in each drug-treated group and the control group. The results are shown in Table 2.

TABLE 2

| | $ED_{50}$ (mg/rat) | | |
|---|---|---|---|
| | 3-Deazaadenosine | Hydrocortisone | Aspirin |
| 3 hr Vol. local (intrapleural) | 0.05 | <0.1 | 0.04 |

EXAMPLE 4

Effects of 3-Deazaadenosine against Adjuvant Arthritis

The effect of 3-deazaadenosine in rats against both developing and established adjuvant arthritis was determined by the method described by R. Vinegar et al., *Journal of Immunopharmacology*, 1, 483 (1979). The scoring procedure of H. L. F. Currey and M. Ziff, J. Exp. Med., 121, 185 (1968) was used to assess the arthritic joint scores of the rats. There were 5 animals in each drug-treated group. For developing adjuvant arthritis the drugs were administered in the diet from day 1 to day 16. For established adjuvant arthritis the drugs were administered from day 21 to day 42. The results are shown in Table 4 below.

TABLE 4

| Drug | Developing Arthritis $ED_{50}$ on Day 16 mg/kg day in diet | Established Arthritis $ED_{25}$ on Day 42 mg/kg/ day in diet |
| --- | --- | --- |
| 3-deazaadenosine | 8 ± 2.8 | (18)* |
| Aspirin | 150 ± 53.1 | <150 |
| Prednisolone | 1 + 0.7 | 0.2 |

*Parentheses indicate an approximate value.

EXAMPLE 5

| Water Soluble Ointment | Amount (g) |
| --- | --- |
| 3-Deazaadenosine | 0.5 |
| Polyethylene glycol 300 | 20.0 |
| Polyethylene glycol 1500 | 79.5 |
| Total | 100.0 |

EXAMPLE 6

| Skin Cream | Amount (g) |
| --- | --- |
| 3-Deazaadenosine | 0.5 |
| Glyceryl monostearate | 20.0 |
| Methylparaben | 0.3 |
| Petrolatum light liquid | 4.0 |
| Propylene glycol | 5.0 |
| Span 60 | 2.0 |
| Tween 61 | 4.0 |
| Water | 64.2 |
| Total | 100.0 |

EXAMPLE 7

| Tablet Formulation | Amount per tablet |
| --- | --- |
| 3-Deazaadenosine | 50 mg |
| Lactose | 85 mg |
| Potato Starch, dried | 14.3 mg |
| Magnesium Stearate | 0.7 mg |
| Total | 150 mg |

EXAMPLE 8

| Syrup | Amount per 10 ml |
| --- | --- |
| 3-Deazaadenosine | 10 mg |
| Glycerine | 1 g |
| Sucrose | 7 g |
| Methyl paraben | 10 mg |
| Sodium Benzoate | 10 mg |

| Syrup | Amount per 10 ml |
| --- | --- |
| Flavour, Cherry | 0.01 ml |
| Colouring | q.s. |
| Water, purified | q.s. to 10 ml |

EXAMPLE 9

| Injection | Amount per Ampoule |
| --- | --- |
| 3-Deazaadenosine | 10 mg |
| Sodium Chloride | 8.5 mg |
| Water for injection | q.s. to 10 ml |

What we may claim may comprise any novel feature disclosed herein, principally but not exclusively for example:

(i) a method for the treatment of inflammation in mammals, including humans suffering from an inflammatory condition, which comprises the administration of an inflammation reducing, non-toxic amount of 3-deazaadenosine or a pharmaceutically acceptable salt thereof;

(ii) 4-amino-1-$\beta$-D-ribofuranosyl-1H-imidazo-[4,5-c]pyridine or a pharmaceutically acceptable salt thereof for use in the treatment of inflammation;

(iii) a pharmaceutical formulation, particularly a topical formulation, comprising 4-amino-1-$\beta$-D-ribofuranosyl-1H-imidazo-[4,5-c]-pyridine or a pharmaceutically acceptable salt thereof together with a pharmaceutically acceptable carrier therefor.

We claim:

1. A method for the treatment of inflammation in mammals suffering from an inflammatory condition which comprises the administration of an inflammation-reducing, non-toxic amount of an active compound selected from the group consisting of 4-amino-1-$\beta$-D-ribofuranosyl-1H-imidazo-[4,5,-c]-pyridine and a pharmaceutically acceptable salt thereof.

2. A method according to claim 1 wherein the active compound is administered in an amount of from about 0.1 to about 10 mg per kg bodyweight per day.

3. A method according to claim 2 wherein the active compound is administered in an amount of about 0.3 to about 1 mg per kilogram bodyweight per day.

4. A method according to claim 1 wherein the inflammatory condition is arthritis.

5. A method according to claim 1 wherein the active compound is administered as a pharmaceutical formulation comprising the active compound together with a pharmaceutically acceptable carrier therefor.

6. A method according to claim 5 wherein the pharmaceutical formulation is in unit dosage form and comprises about 50 mg of the active compound.

7. A method according to claim 5 wherein the formulation is a topical formulation.

8. A topical pharmaceutical formulation for use as an anti-inflammatory agent comprising an effective anti-inflammatory amount of 4-amino-1-$\beta$-D-ribofuranosyl-1H-imidazo-[3,4,-c]-pyridine or a pharmaceutically acceptable salt thereof as the active ingredient, within a pharmaceutically acceptable semi-solid carrier therefor.

9. A topical formulation according to claim 8 wherein the active ingredient is present in an amount of from about 0.01 to about 10% w/w.

10. The method of claims 1, 2, 3, 4, or 5 in which the mammal is a human.

* * * * *